US012161318B2

(12) United States Patent
Samuel et al.

(10) Patent No.: US 12,161,318 B2
(45) Date of Patent: Dec. 10, 2024

(54) RE-TENSIONABLE SUTURE ANCHOR SYSTEM AND RELATED METHODS

(71) Applicant: Dunamis Medical Technologies, LLC, Greenville, AL (US)

(72) Inventors: Forrest Samuel, Carlsbad, CA (US); Prithviraj Chavan, Greenville, AL (US)

(73) Assignee: Dunamis Medical Technologies, LLC, Greenville, AL (US)

( * ) Notice: Subject to any disclaimer, the term of this patent is extended or adjusted under 35 U.S.C. 154(b) by 0 days.

(21) Appl. No.: 17/540,057

(22) Filed: Dec. 1, 2021

(65) Prior Publication Data

US 2022/0167962 A1 Jun. 2, 2022

Related U.S. Application Data

(60) Provisional application No. 63/119,960, filed on Dec. 1, 2020.

(51) Int. Cl.
*A61B 17/04* (2006.01)

(52) U.S. Cl.
CPC .. *A61B 17/0401* (2013.01); *A61B 2017/0414* (2013.01); *A61B 2017/0441* (2013.01); *A61B 2017/045* (2013.01); *A61B 2017/0462* (2013.01)

(58) Field of Classification Search
CPC ........ A61B 17/0401; A61B 2017/0414; A61B 2017/0441; A61B 2017/045; A61B 2017/0446–0462
See application file for complete search history.

(56) References Cited

U.S. PATENT DOCUMENTS 5,791,899 A * 8/1998 Sachdeva ............. A61C 8/0065
433/173
5,849,004 A * 12/1998 Bramlet ............. A61B 17/0401
606/310

(Continued)

OTHER PUBLICATIONS

PCT International Search Report and Written Opinion of the International Searching Authority, PCT/US2019/032037, mailed Jul. 22, 2019.

(Continued)

*Primary Examiner* — Katherine H Schwiker
*Assistant Examiner* — Zehra Jaffri
(74) *Attorney, Agent, or Firm* — Jay B. Bell

(57) ABSTRACT

A system and method comprising an anchor assembly including an anchor and a locking element, a tensionable fixation member (e.g., surgical suture, tape, etc.), and a release member, wherein the anchor further comprises a first end, second end and anchor body. The anchor is configured for implantation into bone. One end of a tensionable fixation member is configured for attachment to a tissue to assist with fixation of the soft tissue. Once the anchor has been seated in bone, the second end of the tensionable fixation member is pulled through a "one-way only" passage in the body of the anchor. When the tensionable fixation member enters passage, it traverses past the locking element positioned within the anchor by bending or deflecting the locking element out of the way to permit passage of the tensionable fixation member while maintaining contact with the tensionable fixation member via elastic compression that results from the elastic bending or deflection of the locking element but prevents the tensionable fixation member from passing back. This continuous locking on the tensionable fixation member creates fixation security, allows for optimal tensioning, and prevents loosening in the opposite direction. The release member may be used to bend or deflect the (Continued)

locking element to loosen the tensionable fixation member to enable an operator to readjust the tension in the tensionable fixation member to the operator's liking.

11 Claims, 12 Drawing Sheets

(56) References Cited

U.S. PATENT DOCUMENTS

| | | | |
|---|---|---|---|
| 5,935,129 A * | 8/1999 | McDevitt | A61F 2/0811 606/232 |
| 5,957,953 A * | 9/1999 | DiPoto | A61B 17/0401 606/313 |
| 6,162,234 A * | 12/2000 | Freedland | A61F 2/0811 606/313 |
| 6,328,758 B1 * | 12/2001 | Tornier | A61F 2/0811 606/232 |
| 6,517,542 B1 * | 2/2003 | Papay | A61F 2/0811 606/232 |
| 6,840,953 B2 | 1/2005 | Martinek | |
| 6,932,834 B2 | 8/2005 | Lizardi et al. | |
| 7,320,701 B2 | 1/2008 | Haut et al. | |
| 7,322,978 B2 * | 1/2008 | West, Jr. | A61B 17/0401 606/232 |
| 7,713,286 B2 | 5/2010 | Singhatat | |
| 7,837,710 B2 * | 11/2010 | Lombardo | A61B 17/0401 606/232 |
| 8,133,258 B2 | 3/2012 | Foerster et al. | |
| 8,137,381 B2 | 3/2012 | Foerster et al. | |
| 8,197,497 B2 | 6/2012 | Nobles et al. | |
| 8,409,252 B2 | 4/2013 | Lombardo et al. | |
| 8,469,998 B2 | 6/2013 | Sojka et al. | |
| 8,545,535 B2 | 10/2013 | Hirotsuka et al. | |
| 8,696,703 B2 | 4/2014 | Anspach, III et al. | |
| 8,882,801 B2 | 11/2014 | DiMatteo et al. | |
| D740,419 S | 10/2015 | Chavan et al. | |
| 9,226,742 B2 * | 1/2016 | Wolf | A61B 17/0401 |
| 9,226,743 B2 | 1/2016 | Dreyfuss et al. | |
| 9,307,979 B1 * | 4/2016 | Bennett | A61B 17/06166 |
| 9,393,006 B2 * | 7/2016 | Housman | A61B 17/861 |
| 9,636,101 B2 * | 5/2017 | Wolf | A61B 17/0401 |
| 9,980,715 B2 * | 5/2018 | Marino | A61F 2/0811 |
| 10,058,317 B2 | 8/2018 | Fan et al. | |
| 10,058,319 B2 | 8/2018 | Konrath et al. | |
| 10,136,883 B2 | 11/2018 | Chan et al. | |
| 10,143,462 B2 * | 12/2018 | Fallin | A61F 2/0811 |
| 10,245,030 B2 | 4/2019 | Gustafson et al. | |
| 10,299,782 B2 | 5/2019 | Sengun et al. | |
| 10,313,618 B2 | 8/2019 | Gustafson et al. | |
| 10,368,857 B2 | 8/2019 | Miller et al. | |
| 10,463,357 B2 | 11/2019 | Gustafson et al. | |
| 10,543,021 B2 * | 1/2020 | Jackson | A61B 17/7037 |
| 10,561,411 B1 * | 2/2020 | Cole | A61F 2/0805 |
| 11,432,812 B2 * | 9/2022 | Chavan | A61B 17/0401 |
| 2001/0008971 A1 * | 7/2001 | Schwartz | A61B 17/0487 606/232 |
| 2003/0105489 A1 * | 6/2003 | Eichhorn | A61F 2/0811 606/232 |
| 2004/0138706 A1 | 7/2004 | Abrams et al. | |
| 2005/0055052 A1 * | 3/2005 | Lombardo | A61B 17/0401 606/232 |
| 2005/0245932 A1 * | 11/2005 | Fanton | A61B 17/0401 606/232 |
| 2006/0241594 A1 | 10/2006 | McCarthy | |
| 2006/0282083 A1 * | 12/2006 | Fanton | A61B 17/0401 606/232 |
| 2007/0233075 A1 | 10/2007 | Dawson | |
| 2007/0270907 A1 | 11/2007 | Stokes et al. | |
| 2008/0275469 A1 * | 11/2008 | Fanton | A61B 17/0487 606/232 |
| 2009/0112270 A1 * | 4/2009 | Lunn | A61B 17/0401 606/301 |
| 2009/0292313 A1 * | 11/2009 | Anspach, III | A61B 17/0401 606/232 |
| 2009/0326579 A1 * | 12/2009 | Anderhub | A61B 17/0401 606/232 |
| 2010/0004683 A1 * | 1/2010 | Hoof | A61B 17/0401 606/232 |
| 2010/0016892 A1 | 1/2010 | Kaiser et al. | |
| 2010/0094355 A1 * | 4/2010 | Trenhaile | A61B 17/0401 606/232 |
| 2010/0121348 A1 * | 5/2010 | van der Burg | A61B 17/888 606/232 |
| 2010/0292733 A1 * | 11/2010 | Hendricksen | A61B 17/0401 606/232 |
| 2011/0112576 A1 * | 5/2011 | Nguyen | A61B 17/0401 606/232 |
| 2012/0035671 A1 * | 2/2012 | Hodge | A61B 17/8685 606/328 |
| 2012/0059417 A1 | 3/2012 | Norton et al. | |
| 2012/0101526 A1 * | 4/2012 | Bennett | A61B 17/0466 606/232 |
| 2013/0006302 A1 | 1/2013 | Paulk | |
| 2013/0096611 A1 * | 4/2013 | Sullivan | A61B 17/0485 606/232 |
| 2013/0103083 A1 | 4/2013 | Baird | |
| 2013/0144334 A1 | 6/2013 | Bouduban et al. | |
| 2013/0197577 A1 * | 8/2013 | Wolf | A61B 17/0401 606/232 |
| 2014/0046369 A1 * | 2/2014 | Heaven | A61B 17/0401 606/232 |
| 2014/0081323 A1 * | 3/2014 | Hawkins | A61B 17/0401 606/232 |
| 2014/0142627 A1 | 5/2014 | Hendricksen | |
| 2014/0277129 A1 * | 9/2014 | Arai | A61B 17/0401 606/232 |
| 2015/0112384 A1 * | 4/2015 | Hirotsuka | A61B 17/0401 606/232 |
| 2015/0119937 A1 * | 4/2015 | Lunn | A61B 17/0401 606/232 |
| 2015/0127048 A1 * | 5/2015 | Curtis | A61B 17/0401 606/232 |
| 2016/0022341 A1 | 1/2016 | Agarwal | |
| 2016/0213370 A1 * | 7/2016 | Chan | A61B 17/0401 |
| 2016/0228117 A1 * | 8/2016 | Borden | A61B 17/0401 |
| 2016/0310127 A1 | 10/2016 | Cavallazzi | |
| 2017/0209135 A1 * | 7/2017 | Sullivan | A61B 17/0483 |
| 2018/0008256 A1 | 2/2018 | Fallin | |
| 2019/0038275 A1 * | 2/2019 | Clark | A61F 2/0811 |
| 2019/0343507 A1 | 11/2019 | Chavan et al. | |
| 2020/0077999 A1 * | 3/2020 | Bowman | A61B 17/06166 |
| 2020/0178953 A1 * | 6/2020 | Da Silva | A61B 17/0482 |
| 2020/0289109 A1 | 9/2020 | Chavan | |
| 2021/0000588 A1 * | 1/2021 | Cain | A61F 2/0811 |
| 2022/0160402 A1 * | 5/2022 | Raju | A61B 17/862 |
| 2022/0354483 A1 * | 11/2022 | Lebens, III | A61B 17/0401 |

OTHER PUBLICATIONS

Voluntary Amendments filed in European Counterpart, EP19800267.7 (NS-PCT of PCT/US2019/032037), Filed Jun. 28, 2021.
Supplemental European Search Report, EP19800267.7 (NS-PCT of PCT/US2019/032037), Mailed Jan. 25, 2022.

* cited by examiner

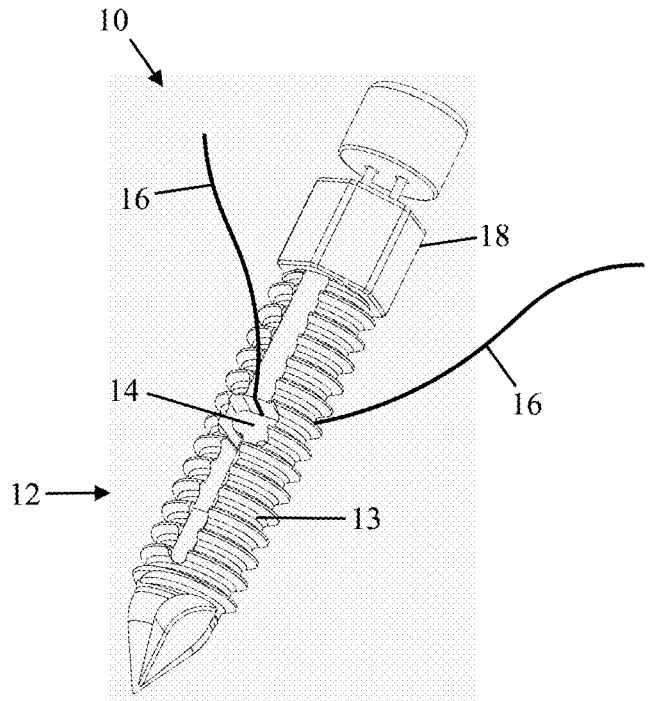
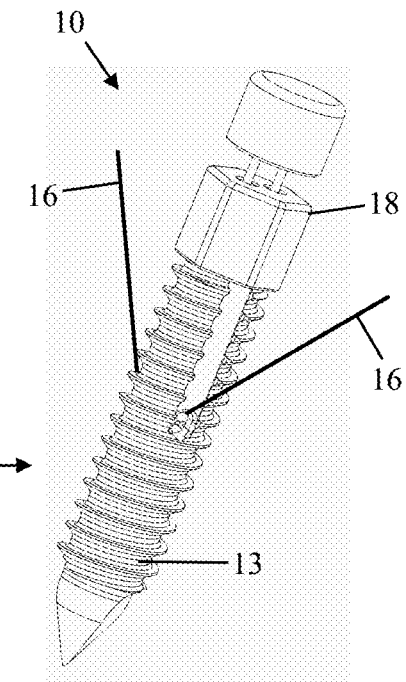
Fig. 1                    Fig. 2
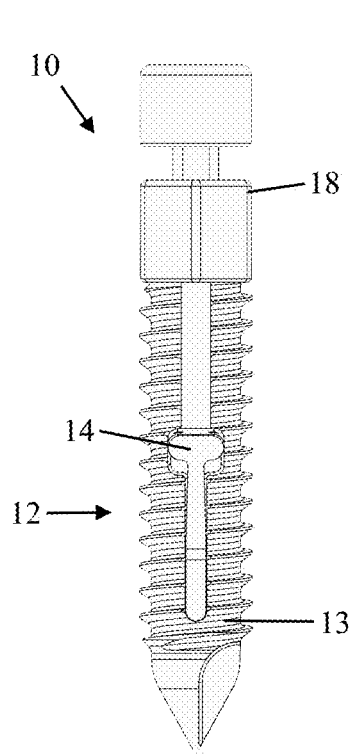
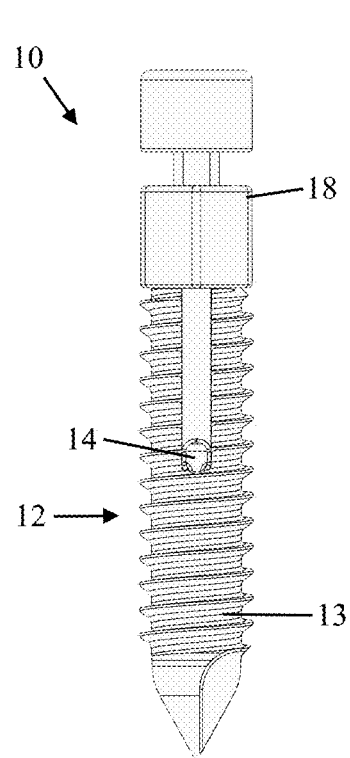
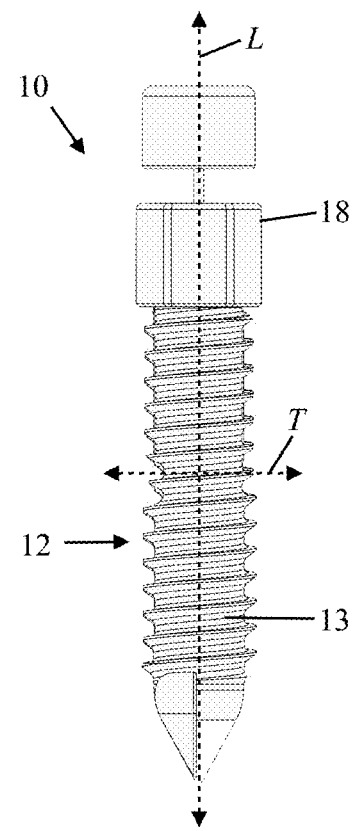
Fig. 3        Fig. 4        Fig. 5

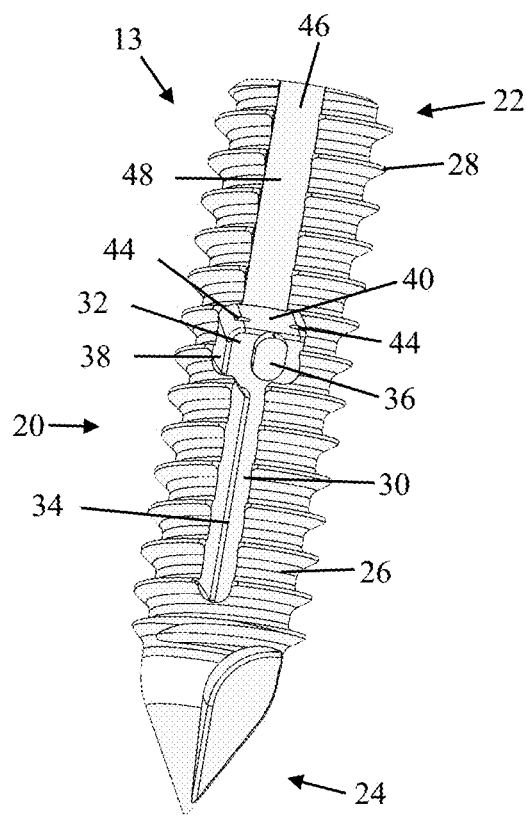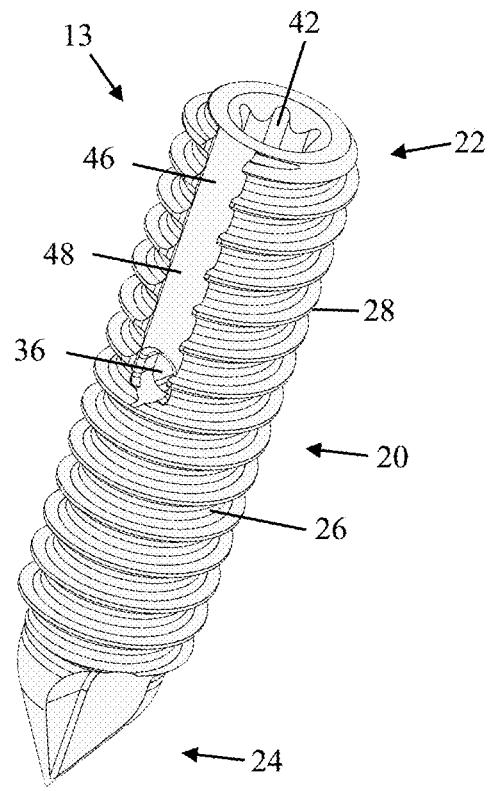
Fig. 8
Fig. 9
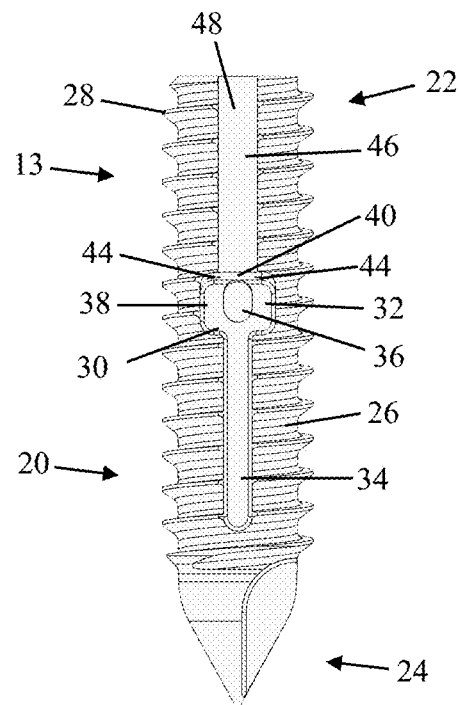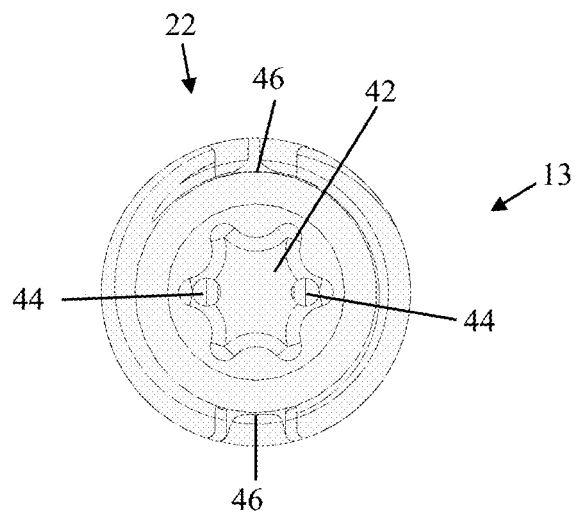
Fig. 10
Fig. 11

RE-TENSIONABLE SUTURE ANCHOR SYSTEM AND RELATED METHODS

CROSS-REFERENCES TO RELATED APPLICATIONS

The present application claims priority under 35 USC 119(e) to U.S. Provisional Patent Application Ser. No. 63/119,960, filed on Dec. 1, 2020 and entitled "RETENSIONABLE LOCKING ANCHOR," the entire contents of which are hereby incorporated by reference into this disclosure as if set forth fully herein.

FIELD

The present invention relates generally to tissue repair, and more specifically, to a knotless anchor assembly and method of securing tissue, ligaments, sutures, grafts, allografts, membrane, gap fillers, tension members or bone to bone in stabilization procedures.

BACKGROUND

Tendon, ligament and joint capsular injuries account for 45% of the orthopedic injuries which seek medical attention. Tendon injuries alone effect 30 million people annually, resulting in an enormous amount of physical and financial burden to both the individuals and the economy. Soft tissue injuries (e.g., rotator cuff tears) are highly relevant among aging population affecting over half of the individuals above the age of 60 years. Most of the affected people are treated with surgical repair or reconstruction to avoid long-term disability and pain relief. Tears can be primary and related to an injury or secondary and related to a re-tear after a primary repair or surgery. There has been an increased incidence of secondary tears and a large proportion of them may be avoided by using a better device to perform the procedure.

Secondary or type 2 failure occurs where the tendon fails medially to the repair, close to the muscle tendon attachment. Secondary medial cuff failure near the muscle tendon attachment after repair (type 2 failure) has been associated with the placement of knots and abrasive suture materials near the muscle tendon attachment, thus, potentially resulting in acute or chronic subacromial knot impingement, medial row stress concentration, tendon strangulation, and/or suture cut-out in this area. When failure occurs, the tendon/muscle is found to be torn medial to the previous repair site of the cuff tendon insertion.

Studies suggest that primary prevention can address secondary type 2 re-tears, and techniques such as utilizing knotless, linked and bridging constructs have been developed to prevent tissue strangulation and improve force distribution. The use of tapes with these knotless repairs also decreases the compressive stress per unit area of tendon. The lack of knots avoids the possibility of acute or chronic postoperative knot impingement within the subacromial space, decreases operative time, and improves efficiency. Studies also suggest that rotator cuff tears that are repaired with a "tension overload mechanism" over a portion of the muscle-tendon units will undergo gradual failure with physiologic cyclic loading. Therefore, tendons should be repaired without tension if possible.

Several factors currently lead to an increased failure of repair. They are mainly a) knots causing impingement, and b) problems related to tensioning of repair, which can lead to strangulation of tissue causing necrosis over time, increased stresses on the anchoring device and failure with suture pulling out through tissue.

Knotless anchors currently in the market only address knot related problems but continue to have other limitations whereby they either must be used in combination with another system, such as a secondary anchor, have limitation of the number of fibers passing through the anchor and continue to have major challenges related to tissue tensioning. These deficiencies hinder the surgeon's ability to adjust tissue tension at the time of repair or readjust once the repair is complete. This leads to under-tensioning and failure due to gap formation or over-tensioning of the repair and failure at repair site, strangulation of blood supply to the tissue and re-tear. In addition to tendon and/or soft tissue re-tears noted above, failure of suture-anchor constructs are also possible, including anchor pull-out, suture breakage, or eyelet breakage. Thus, a need exists for a knotless anchor assembly and system that doesn't require a secondary anchor and allows for tension adjustment at the time of repair.

SUMMARY

Knotless anchors in the prior art hinder surgeons' ability to adjust tissue tension at the time of repair or readjust once the repair is complete resulting in under tensioning and failure due to gap formation or over-tensioning of the repair and failure at repair site, strangulation of blood supply to the tissue and re-tear. The re-tensionable anchor system and related methods disclosed herein allows the surgeon to adjust the repair tension based on the tissue biology of the tendon and, hence, optimizes the mechanical construct of the repair by providing a stable tension free repair. This reduces failures of repair due to inappropriate soft tissue tensioning. Further, surgical cost will be reduced due to decreasing the number of devices needed for the procedure, as the knotless anchor assembly can be used independently and does not require other systems or anchors. The re-tensionable anchor system allows more sutures to pass through the anchor body and reduces the operative time since it eliminates the need for knot tying.

The system and method of the present disclosure comprises an anchor assembly including an anchor and a locking element, a tensionable fixation member (e.g., surgical suture, tape, etc.), and a release member, wherein the anchor further comprises a first end, second end and anchor body. This re-tensionable anchor is designed to be implanted into bone. One end of the tensionable fixation member is attached to the tissue on one end to assist with fixation of soft tissue. Once the anchor has been seated in the bone, the second end of the tensionable fixation member is pulled through a "one-way only" passage in body of the anchor. When the tensionable fixation member enters the body of the anchor, it traverses past by bending or deflecting out of the way a locking element within the anchor that will permit passage of the tensionable fixation member and will stay in contact with the fixation member via elastic compression that results from the elastic bending or deflection but prevent it from passing back. This continuous locking on the tensionable fixation member creates fixation security, allows for optimal tensioning, and prevents loosening in the opposite direction. An instrument designed to reach the locking element and deliberately bend or deflect it will allow for loosening of the tensionable fixation member to provide for the ability to readjust the tension to the operator's liking.

The anchor may be made out of any material commonly used or can be theoretically used to create an anchor device e.g. peek, suture based metal, composite etc. The anchor may be self-tapping or may require an additional tool to implant.

The anchor body may be implanted using a screw-in mechanism or a push-in mechanism. The tensionable fixation members can be sutures, tapes or any material that can be used to hold the soft tissue or bony structure that is being fixed. The device may self-locking or have a secondary mechanism to initiate or augment locking.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein:

FIG. 1 is a perspective view of an example of a re-tensionable anchor system of the present disclosure, according to some embodiments;

FIG. 2 is another perspective view of the re-tensionable anchor system of FIG. 1, according to some embodiments;

FIG. 3 is a side view of the re-tensionable anchor system of FIG. 1, according to some embodiments;

FIG. 4 is another side view of the re-tensionable anchor system of FIG. 1, rotated 180° from the view of FIG. 3, according to some embodiments;

FIG. 5 is another side view of the re-tensionable anchor system of FIG. 1, rotated 90° from the view of FIG. 3, according to some embodiments;

FIG. 8 is a perspective view of an example of an anchor forming part of the re-tensionable anchor system of FIG. 1, according to some embodiments;

FIG. 9 is another perspective view of the anchor of FIG. 8, according to some embodiments;

FIG. 10 is a plan view of one side of the anchor of FIG. 8, according to some embodiments;

FIG. 11 is a plan view of the proximal end of the anchor of FIG. 8, according to some embodiments;

DETAILED DESCRIPTION OF A PREFERRED EMBODIMENT

Figure 6:
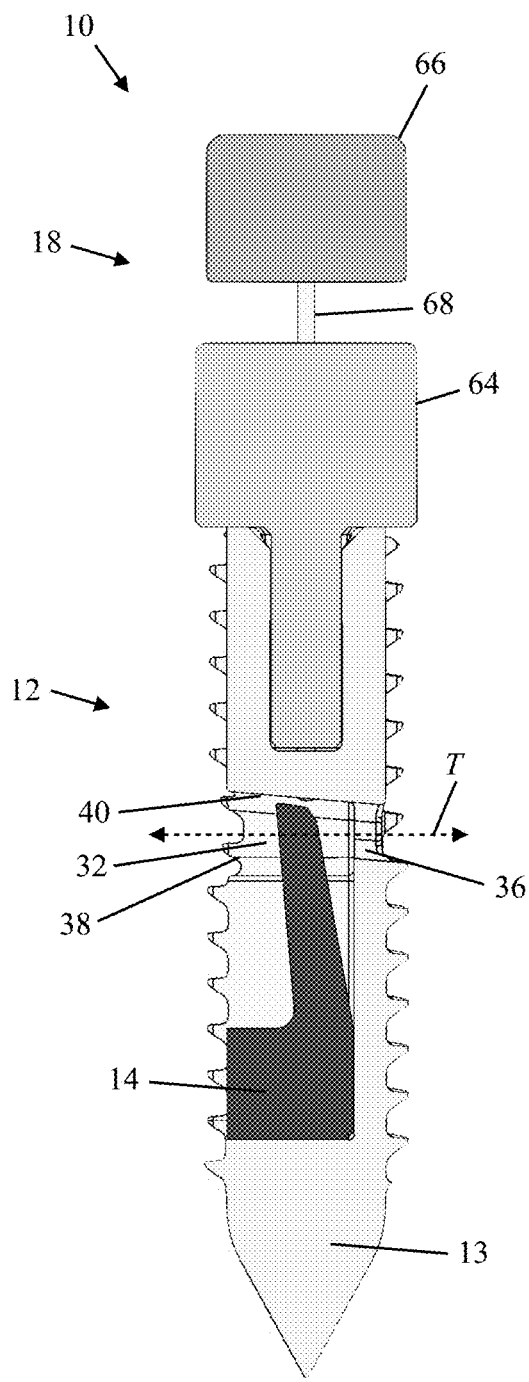
FIG. 6 is a sectional view of the re-tensionable anchor system of FIG. 1, according to some embodiments.
Figure 7:
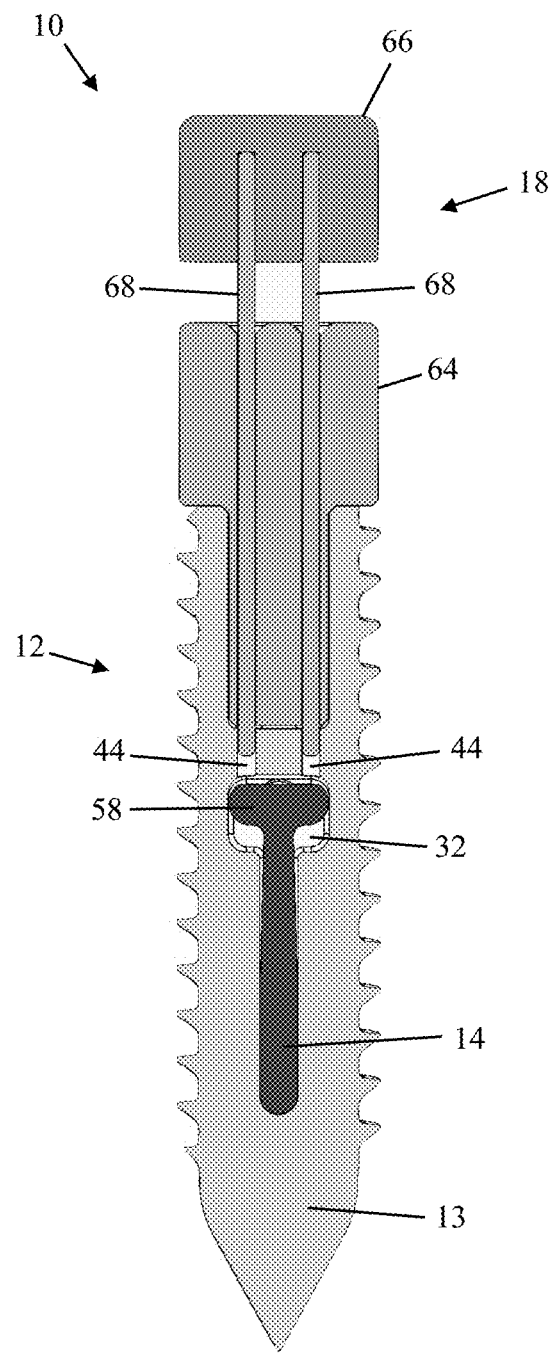
FIG. 7 is another sectional view of the re-tensionable anchor system of FIG. 1, rotated 90° from the view of FIG. 6, according to some embodiments.
Figure 12:
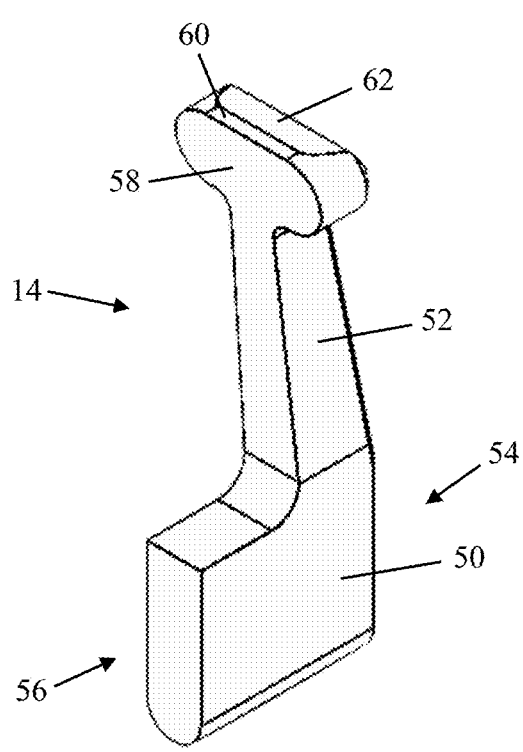
FIG. 12 is a perspective view of an example of a locking element forming part of the re-tensionable anchor system of FIG. 1, according to some embodiments.
Figure 13:
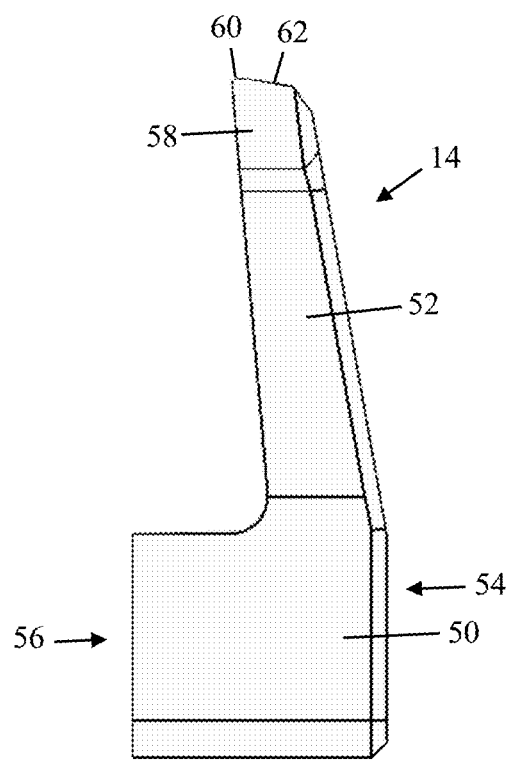
FIG. 13 is a side plan view of the locking element of FIG. 12, according to some embodiments.
Figure 14:
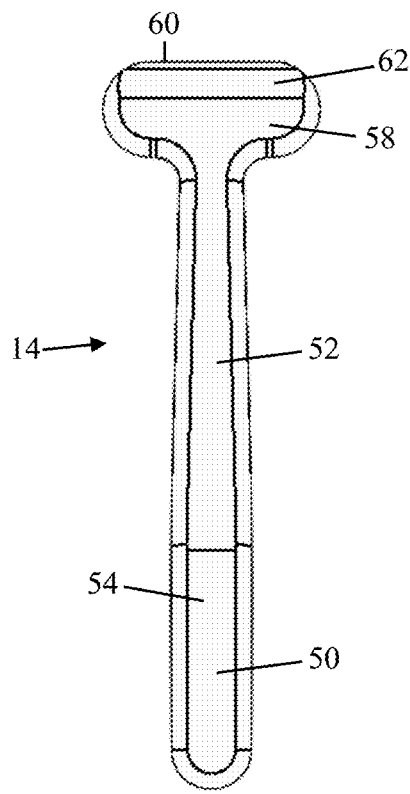
FIG. 14 is a plan view of a first end of the locking element of FIG. 12, according to some embodiments.
Figure 15:
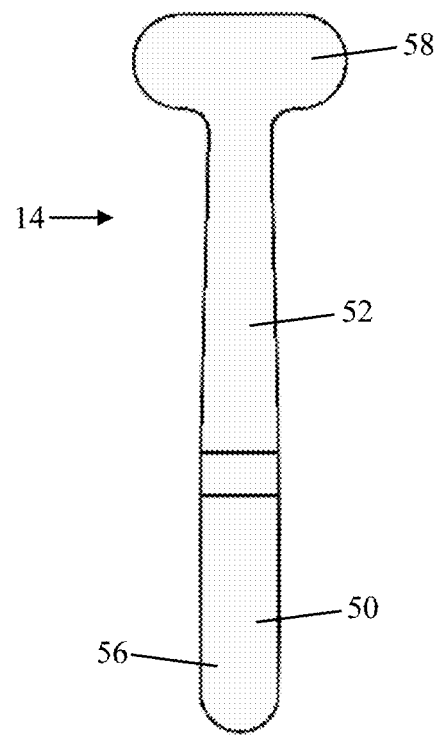
FIG. 15 is a plan view of a second end of the locking element of FIG. 12, according to some embodiments.
Figure 16:
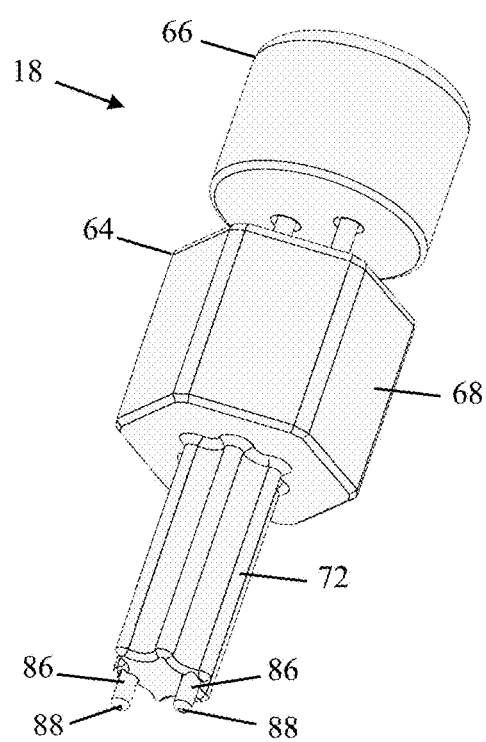
FIGS. 16-23 illustrate an example of a release member forming part of the re-tensionable anchor system of FIG. 1, according to some embodiments.
Figure 17:
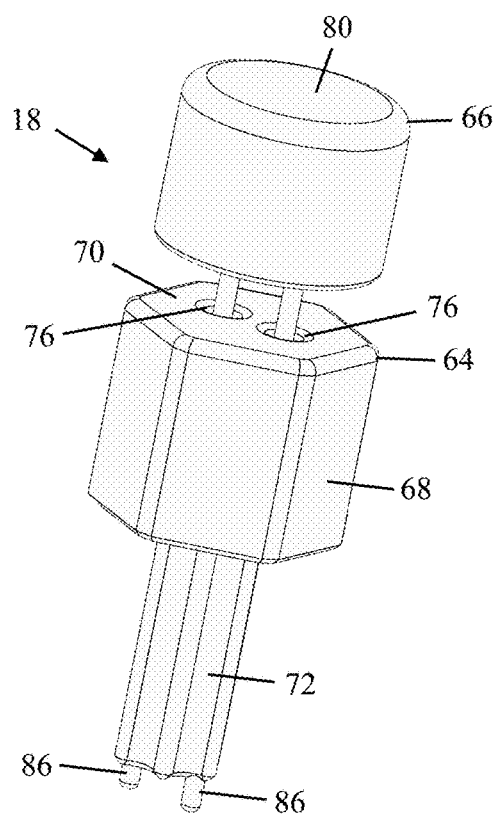
Figure 18:
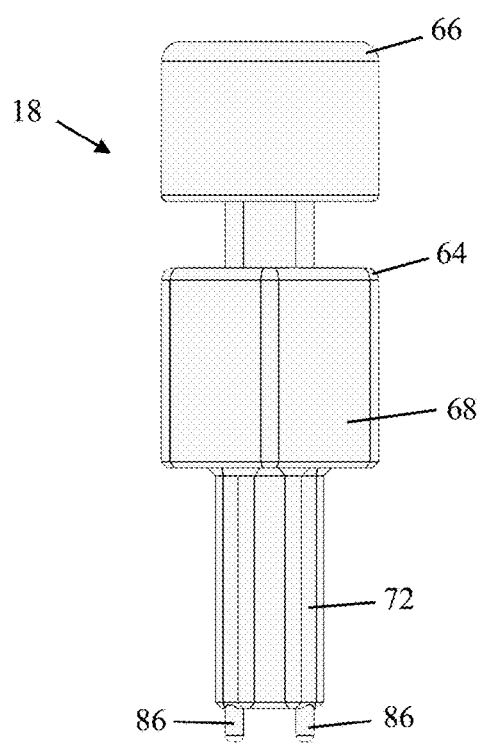
Figure 19:
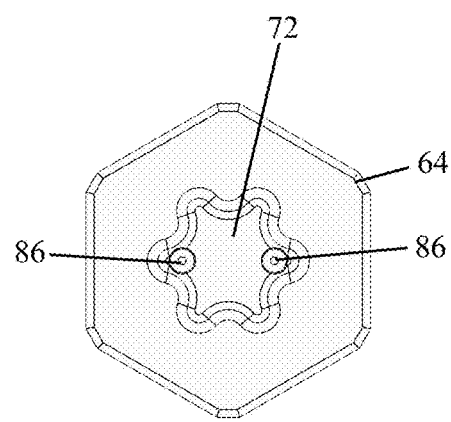
Figure 20:
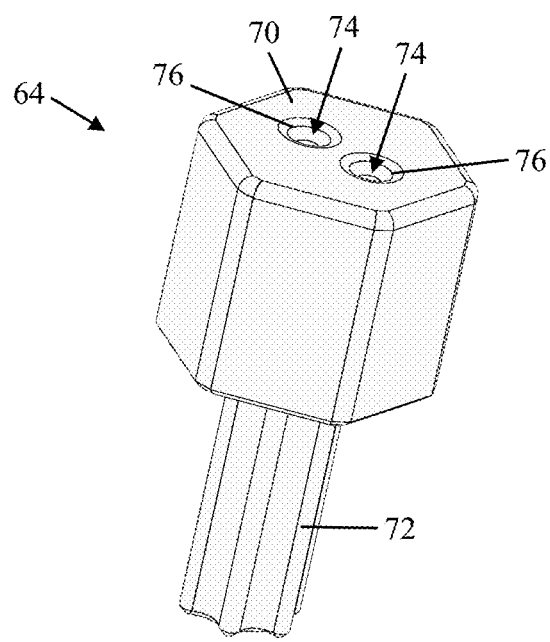
Figure 21:
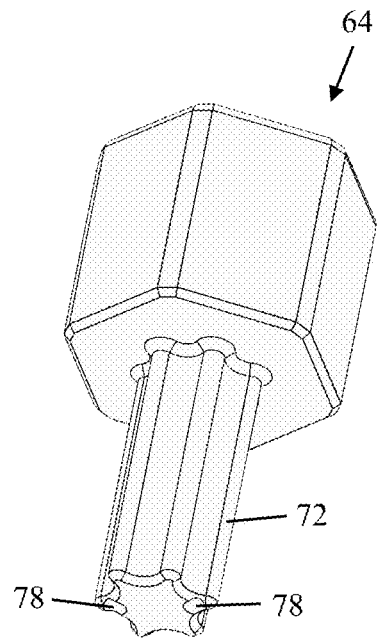
Figure 22:
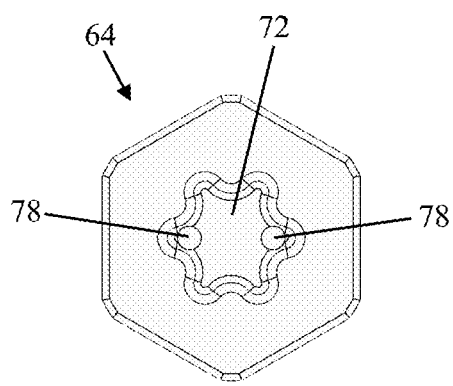
Figure 23:
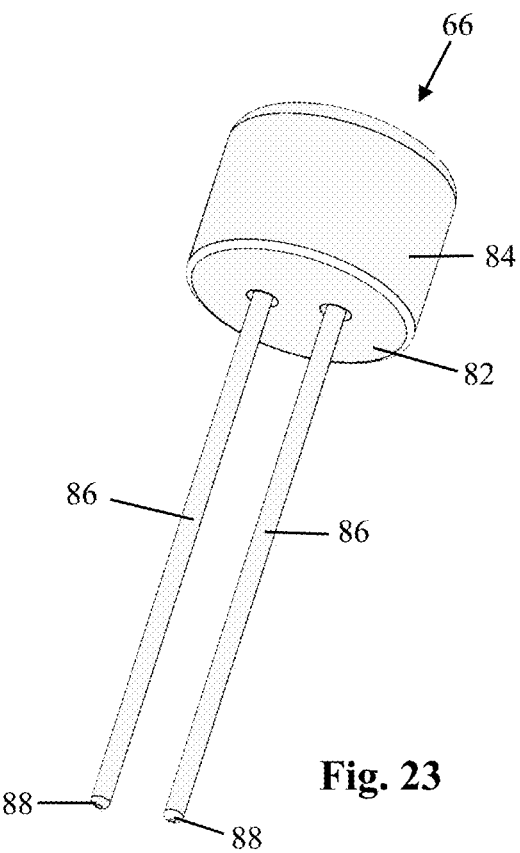

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The re-tensionable anchor system and related methods disclosed herein boasts a variety of inventive features and components that warrant patent protection, both individually and in combination.

FIGS. 1-7 illustrate an example of a re-tensionable anchor system 10 according to some embodiments of the present disclosure. In some embodiments, the re-tensionable anchor system 10 may include an anchor assembly 12 including an anchor 13 and a locking element 14 positioned within the anchor 13, a tensionable fixation member 16, and a release member 18. In some embodiments, the anchor assembly 12 is configured to releasably secure a tensionable fixation member 16 passing through the anchor assembly 12 such that the tensionable fixation member 16 may be advanced through the anchor assembly 12 in one direction and prevented from retreating through the anchor assembly 12 in an opposite direction. By way of example, the re-tensionable anchor system 10 of the present disclosure may be used in surgical procedures to secure soft tissue to bone. In some embodiments, the anchor assembly 12 may be secured to bone by way of a threaded engagement or push-in engagement. In some embodiments, the tensionable fixation member 16 may comprise a surgical suture, tape, or other fixation member configured to be longitudinally stretched or strained to achieve a desired degree of tension therein. In some embodiments, the tensionable fixation member 16 is a flexible fixation member. By way of example only, one end of the tensionable fixation member 16 may be attached to or coupled with a soft tissue being repaired. In some embodiments, once the anchor assembly 12 has been inserted into bone to which the soft tissue is to be secured, the other/loose/free end of the tensionable fixation member 16 may be advanced or shuttled through a transverse passage in the anchor 13. As will be explained below, the locking element 14 in a "locked" state allows for unidirectional insertion through the transverse passage, while preventing movement of the tensionable fixation member 16 in the opposite direction. In this manner, the locking element 14 allows for the tension in the tensionable fixation member 16 to be increased by pulling on the tensionable fixation member 16 in the insertion direction while preventing loosening of the tensionable fixation member 16. In some embodiments, an attachable release member 18 may be employed to act on the locking element 14 to disengage the locking element 14 from the tensionable fixation member 16, enabling a release of tension in the event that the user determines that an adjustment of tension is needed. In some embodiments, the release member 18 may be part of an insertion tool or may be an independent attachment that is temporarily coupled with the anchor assembly 12 to enable adjustment of the tensionable fixation member 16 during the surgical procedure.

FIGS. 8-11 illustrate an example of an anchor 13 forming part of the anchor assembly 12 according to some embodiments of the present disclosure. By way of example only, the anchor 13 comprises a generally cylindrical body 20 having a proximal end 22, a distal end 24, and a central longitudinal axis L extending through the proximal and distal ends (as shown by way of example in FIG. 5). In some embodiments, the outer surface 26 of the body 20 may have a bone engaging feature 28 including but not limited to helical threads 28 (as shown by way of example in FIGS. 1-10), annular ridges, bumps, spikes, roughening, or other surface treatment that improves purchase of the anchor 13 within bone. In some embodiments, the outer surface 26 may be smooth or untreated.

By way of example, the anchor body 20 further comprises a central cavity 30 formed therein near the longitudinal middle of the anchor body 20 between the proximal and distal ends 22, 24. In some embodiments, the central cavity 30 comprises a transverse passage 32 sized and configured to receive the proximal portion 58 of the deflectable flange 52 of the locking element 14, and an elongated longitudinal recess 34 extending distally from the transverse passage 32. By way of example, the transverse passage 32 extends through the anchor body 20 along an axis T that is generally transverse to the longitudinal axis L of the anchor body 20 (See FIG. 5). In some embodiments, the central cavity 30 further comprises a first (or "ingress") opening 36 formed on a first side of the cavity 30 along the transverse axis T and a second (or "egress") opening 38 formed on a second side of the central cavity 30 along the transverse axis T and opposite the ingress opening 36. In some embodiments, the central cavity 30 further comprises a proximal wall or "ceiling" 40 forming the proximal boundary of the transverse passage 32. In some embodiments, the proximal wall 40 comprises a smooth angled surface. In some embodiments, the proximal wall 40 comprises a textured angled surface. As shown by way of example in FIG. 6, the angled surface of the proximal wall 40 may be angled relative to the transverse axis T such that the portion of the proximal wall 40 near the ingress opening 36 is distal of the portion of the proximal wall 40 near the egress opening 38. As will be explained below, the angled surface of the proximal wall 40 interacts with the proximal portion 58 of the deflectable flange 52 of the locking element 14 to: a) create a unidirectional or "one-way" path through the transverse passage 32 for the tensionable fixation member 16 and b) create a "pinch point" at which the tensionable fixation member 16 may be captured or secured between the proximal edge 60 of the deflectable flange 52 and the proximal wall 40 of the anchor body 20.

In some embodiments, the proximal end 22 may include a driver recess 42 formed in the interior of the anchor body 20 along the longitudinal axis and extending at least partially along the length of the anchor body 20. By way of example, the driver recess 42 may be sized and shaped to receive a shaped end of an insertion tool to enable the tool to apply a rotational torque (for example) to the anchor 13 to drive the anchor assembly 12 into bone. By way of example, the driver recess 42 has a termination proximal of the central cavity 30 such that the driver recess 42 does not intersect the central cavity 30. In some embodiments, the anchor body 20 may further include one or more longitudinal apertures 44 extending proximally between the central cavity 30 (e.g. through the proximal wall 40) and the driver recess 42. In some embodiments, the one or more longitudinal apertures 44 may be sized and configured to enable passage of the elongated prongs 86 of the release member 18 therethrough, so that the prongs 86 may contact the proximal portion 58 of the locking element 14 to move the proximal portion from a locked position to an unlocked position and thereby enabling retensioning of the tensionable fixation member 16.

In some embodiments, the anchor 13 may comprise a first outer recess or thread break 46 on the outer surface 26 extending linearly between the ingress opening 36 and the proximal end 22, and a second outer recess or thread break 46 on the outer surface 26 extending linearly between the egress opening 38 and the proximal end 22. By way of example, the outer recesses 46 each have a smooth surface 48 interrupting the threads or other bone engaging feature 28. In some embodiments, the outer recesses 46 are sized to slideably receive at least a portion of the tensionable fixation member 16 therein when the anchor assembly 12 is implanted in bone (e.g., FIGS. 24-25). This feature enables retensioning or adjustment of the tensionable fixation member 16 upon release of the locking element 14 by the release member 18 during the procedure while also reducing or preventing shearing of the tensionable fixation member 16 by the bone engaging features 28 (e.g. threads 28) of the anchor 13.

FIGS. 12-15 illustrate an example of a locking element 14 forming part of the anchor assembly 12 according to some embodiments of the present disclosure. By way of example, the locking element 14 may comprise a base 50 and a deflectable flange 52 extending proximally from the base 50. In some embodiments, the base 50 may be sized and shaped to fit snugly within the longitudinal recess 34 of the central cavity 30 of the anchor 13 to securely and immovably couple the locking element 14 and the anchor 13. In some embodiments, the base 50 may be immovably secured to the longitudinal recess 34 by any suitable securement method or methods known in the art, including but not limited to (and by way of example only) a form fit engagement, press fit engagement, snap fit engagement, adhesive, pin, and/or screw. In some embodiments the deflectable flange 52 may be integrally formed with the anchor 13. The base 50 includes a first end 54 and a second end 56. In some embodiments, the deflectable flange 52 extends from the first end 54 of the base 50 and is angled toward the second end 56. The flange 52 has some elasticity in that the flange 52 is deflectable in the direction of the second end 56 of the base 50 but is biased to return to its original position. In this manner, the flange 52 may be temporarily deflected by force (e.g. by prongs 86 of the release member 18 or by advancing the tensionable fixation member 16 through the transverse passage 32 in the insertion direction) and then returned to its original position to capture or recapture the flexible fixation member 16. By way of example, the base 50 is coupled with the anchor 13 such that the first end 54 is positioned proximate the ingress opening 36 and the second end 56 is positioned proximate the egress opening 38, and the deflectable flange 52 is therefore biased toward the egress opening 38, as shown for example in FIG. 6.

By way of example, the locking element 14 further includes a proximal portion 58 comprising a shaped end sized to be moveably located within the transverse passage 32 of the central cavity 30 and to also engage with the tensionable fixation member 16. In some embodiments, the proximal portion 58 further includes a proximal edge 60 which cooperates with the proximal wall 40 of the central cavity 30 to capture the tensionable fixation member 16 therebetween thereby forming a pinch point. In some embodiments, the proximal portion 58 includes a beveled surface or chamfer 62 extending from the proximal edge 60 toward the first end 54 of the base 50. By way of example, the beveled surface 60 provides an angled engagement surface for the tensionable fixation member 16 and/or shuttle member 90 (See e.g., FIGS. 25-26) such that as the tensionable fixation member 16 and/or shuttle member 90 is advanced through the transverse passage 32 in the insertion direction and contacts the beveled surface 62, the tensionable fixation member 16 and/or shuttle member 90 forces the deflectable flange 52 to deflect toward the second end 56 of the base 50, increasing the distance between the proximal edge 60 of the flange 52 and the proximal wall 40 of the central cavity 30 and thereby enabling unidirectional translation of the tensionable fixation member 16 and/or shuttle member 90 past the locking element 14.

Figure 24:
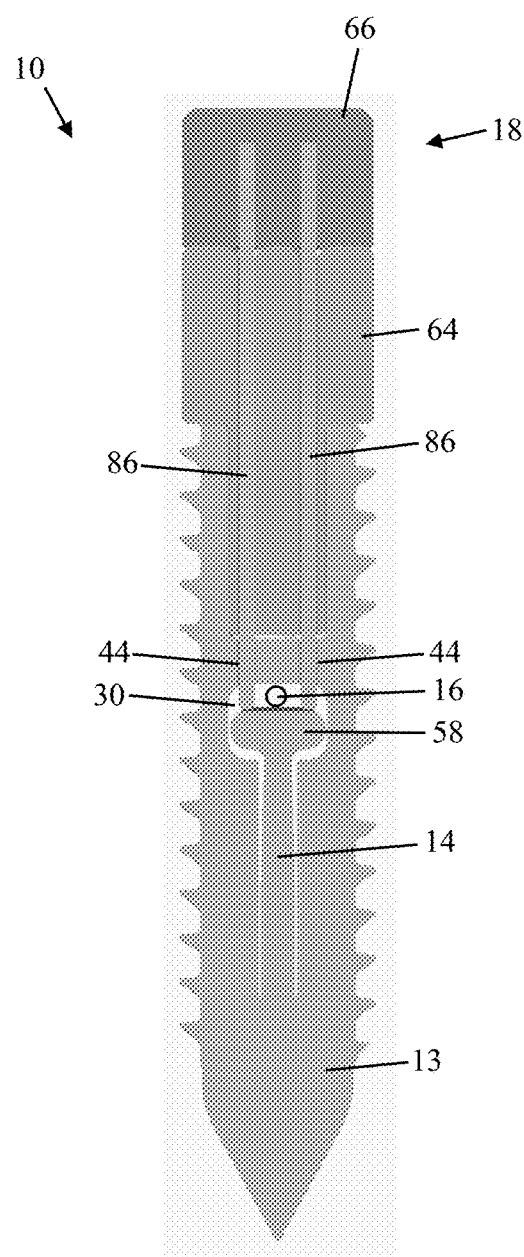
FIG. 24 is a cross-sectional view of the re-tensionable anchor system of FIG. 1, showing the locking element in an unlocked position, according to some embodiments.

In addition, the beveled surface 60 provides an angled engagement surface for the prongs 86 of the release member 18, such that as the prongs 86 advance and contact the beveled surface 62, the prongs 86 force the deflectable flange 52 to deflect toward the second end 56 of the base 50, increasing the distance between the proximal edge 60 of the flange 52 and the proximal wall 40 of the central cavity 30 and thereby releasing the tensionable fixation member 16 from the locking element 14, which enables retensioning of the tensionable fixation member 16 as needed, for example by translating the tensionable fixation member 16 in the opposite direction (e.g., toward the ingress opening) (See, e.g., FIG. 24). As the prongs 86 retreat through the longitudinal apertures 44, the deflectable flange 52 returns to its original position, capturing (or recapturing) and locking the tensionable fixation member 16 between the proximal edge 60 and the proximal wall 40. Once the tensionable fixation member 16 is so captured, any pulling force exerted in the opposite direction (e.g., toward the ingress opening) causes the tensionable fixation member 16 to pull the deflectable flange 52 in the same direction, which due to the angled orientation the proximal wall 40 decreases the distance between the proximal edge 60 and the proximal wall 40, and increasing the compressive force applied to the tensionable fixation member 16.

FIGS. 16-24 illustrate an example of a release member 18 forming part of the re-tensionable anchor system 10 according to some embodiments of the present disclosure. In some embodiments, the release member 18 may be integral with a distal end of an insertion tool. In some embodiments, the release member 18 may be independent of an insertion tool. In some embodiments, the release member 18 may be temporarily coupled to the anchor assembly 12 and removed prior to completion of the surgical procedure.

In some embodiments, the release member 18 comprises a base 64 (e.g., which may be a distal tip of an insertion instrument) and a button 66 that is moveably coupled with the base 64. By way of example only, the base 64 may include a lateral surface 68, a proximal surface 70, a coupling extension 70, and one or more longitudinal channels 72 extending through the base 64 and/or coupling extension 70. In some embodiments, the lateral surface 68 may be contoured or shaped to enable a user to apply rotational torque to the release member, for example if necessary to turn the anchor 13. In some embodiments, the proximal surface 70 may be generally planar and includes the proximal openings 76 of the longitudinal channels 74. In some embodiments, the coupling extension 72 extends distally from the base 64 and is sized and shaped to slidingly engage with the driver recess 42 of the anchor 13. The longitudinal channels 74 are sized and shaped to enable passage of the one or more prongs 86 therethrough. In some embodiment, the distal end of the coupling extension 72 includes the distal openings 78 of the longitudinal channels 74. Notably, when the release member 18 is coupled with the anchor 13, the distal openings 78 of the coupling extension 72 are aligned with the longitudinal apertures 44 of the anchor 13 so that the distal tips 88 of the prongs 86 may pass through the longitudinal aperture 44 and into the central cavity 30 of the anchor 13 (See, e.g., FIG. 24).

In some embodiments, the button 66 may include a proximal surface 80, a distal surface 82, a lateral surface 84, and one or more prongs 86 extending distally from the distal surface 82. By way of example, the one or more prongs 86 each include a distal tip 88 that may be rounded or curved to facilitate translational interaction with the proximal beveled surface 62 of the locking element 14, as described above. In some embodiments (e.g., including the embodiment shown in the attached Figures), the button 66 may have two prongs 86 spaced apart, however any number of prongs may be used. In the example shown, the two prongs 86 are spaced apart by a distance sufficient to enable passage of the tensionable fixation member 16 between the prongs 86, for example when the prongs 86 are engaged with the proximal portion 58 of the locking element 14. For example, this enables free movement (e.g., forward or backward) of the tensionable fixation member 16 when the prongs 86 have deflected the locking element 14 into an unlocked position, enabling the user to ensure the tensionable fixation member 16 has the desired amount of tension applied. It should be noted that the number, spacing, and positioning of the longitudinal channels 74 coincides with the number, spacing, and positioning of the prongs 86.

Figure 32:
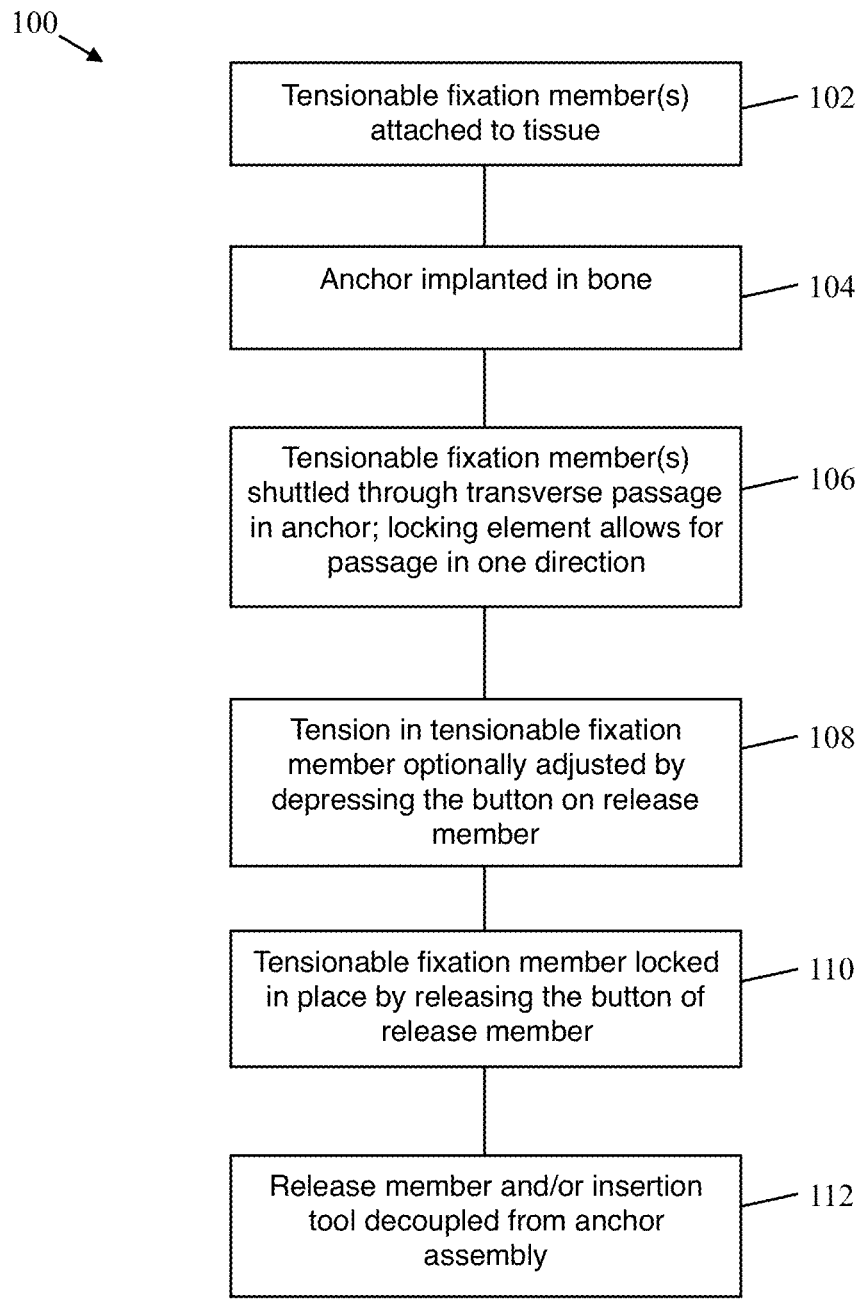
FIG. 32 is a flowchart depicting several example steps of a method of attaching a tissue to bone using the re-tensionable anchor system of FIG. 1, according to some embodiments.

By way of example only, FIGS. 25-31 depict several steps of a method 100 of adjustably anchoring one or more surgical sutures or other tensionable fixation members 16 during a tissue repair surgery (for example), in which a tissue 5 is secured to a bone 7. FIG. 32 is a flowchart presenting several steps of the method 100. It should be noted that the example described herein and shown in the attached Figures depicts a single tensionable fixation member 16 in use with the anchor assembly 12. However, in some embodiments, multiple tensionable fixation members 16 may be used with a single anchor assembly 12 in a same or similar manner to strengthen the surgical repair, and therefore it should be understood that any description of a single tensionable fixation member 16 used herein also includes a plurality of tensionable fixation members 16.

Figure 25:
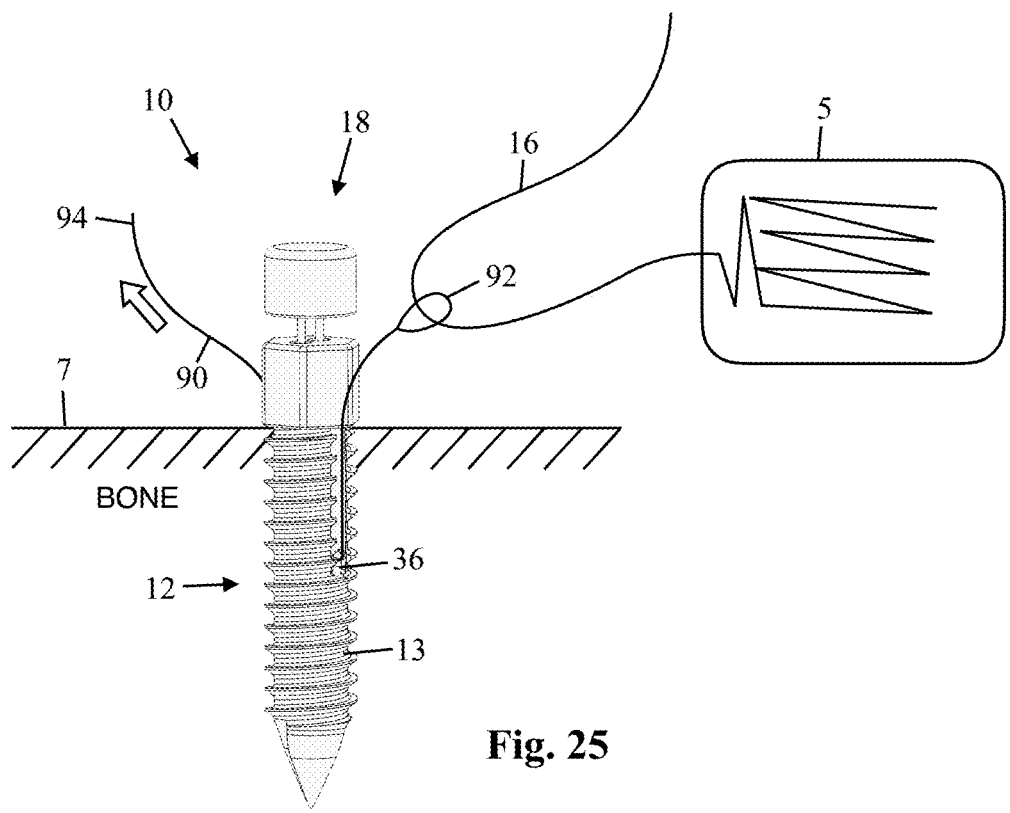
FIGS. 25-31 are perspective view of example steps of a method of attaching a tissue to bone using the re-tensionable anchor system of FIG. 1, according to some embodiments.

Referring to FIGS. 25 and 32, in some embodiments, a first step 102 in the method 100 is to attach one or more tensionable fixation members 16 to a tissue 5 to be repaired (e.g., after opening an operative wound to provide access to the surgical target site). In some embodiments, the next step 104 is to implant an anchor assembly 12 into a bone 7 in a desired location to secure the tissue 5. In some embodiments, a shuttle member 90 may be preloaded into the anchor assembly 12, or alternatively may be coupled with the anchor assembly 12 after implanting the anchor assembly 12 into bone. By way of example, the shuttle member 90 is coupled with the anchor assembly 12 by passing the shuttle member 90 through the transverse passage 32 from the ingress opening 36 to the egress opening 38 such that a coupling end 92 of the shuttle member 90 extends away from the ingress opening 36 of the anchor 13 and a free end 94 of the shuttle member 90 extends away from the egress opening 38 of the anchor 13, as shown by way of example only in FIG. 25.

Figure 26:
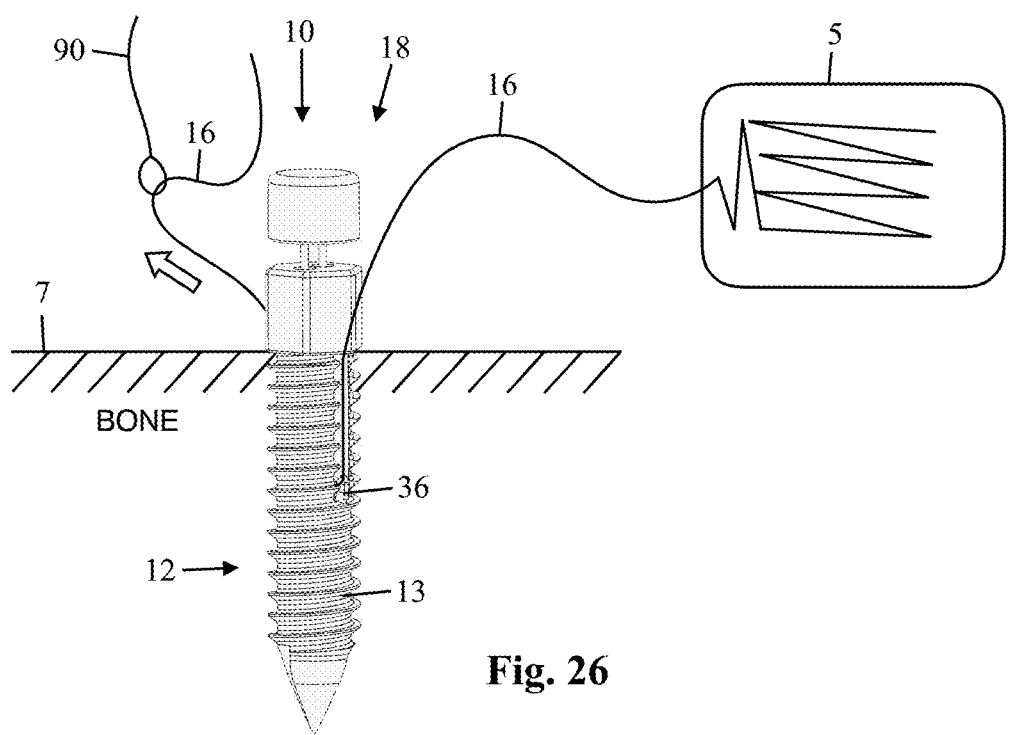

In some embodiments, the next step 106 of the method 100 is to shuttle the tensionable fixation member 16 through the transverse passage 32 of the anchor assembly 12 to couple the tensionable fixation member 16 with the anchor assembly 12, as shown by way of example in FIG. 26. To accomplish this, the tensionable fixation member 16 may be first coupled with the coupling end 92 of the shuttle member 90, and then the free end 94 may be pulled by a user away from the egress opening 38, pulling the tensionable fixation member 16 through the transverse passage 32 to couple the tensionable fixation member 16 to the anchor assembly 12. In some embodiments, this step may be accomplished with the locking element 14 in an initial or "locked" position because the locking element 14 allows for one-way advancement of the shuttle member 90 and or tensionable fixation member 16 through the transverse passage 32 as described above. In some embodiments, this step may be accomplished with the release member 18 depressed and the locking element 14 in the unlocked position so that the tensionable fixation member 16 may move freely within the transverse passage 32, however it may be preferable to utilize the unidirectional nature of the locking element 14 to maintain a minimum tension in the tensionable fixation member 16 during use.

Once the tensionable fixation member 16 has been coupled with the anchor assembly 12, the user may exert a pulling force on the tensionable fixation member to pull the tissue 5 toward the bone 7 and/or a create a desired amount of tension in the tensionable fixation member 16. Due to the unidirectional nature of the locking element 14, pulling on the tensionable fixation member 16 in the direction of the egress opening 38 (e.g., the first direction or direction of insertion) causes the tensionable fixation member 16 to advance through the transverse passage 32 (if possible) and/or increases the tension in an already taut tensionable fixation member 16. However, pulling in the opposite direction or the direction of the ingress opening 36 (e.g., the second direction or direction of release) causes the tensionable fixation member 16 to be pinched harder between the locking element 14 and the proximal wall 40 of the central cavity 30, as described above.

Figure 27:
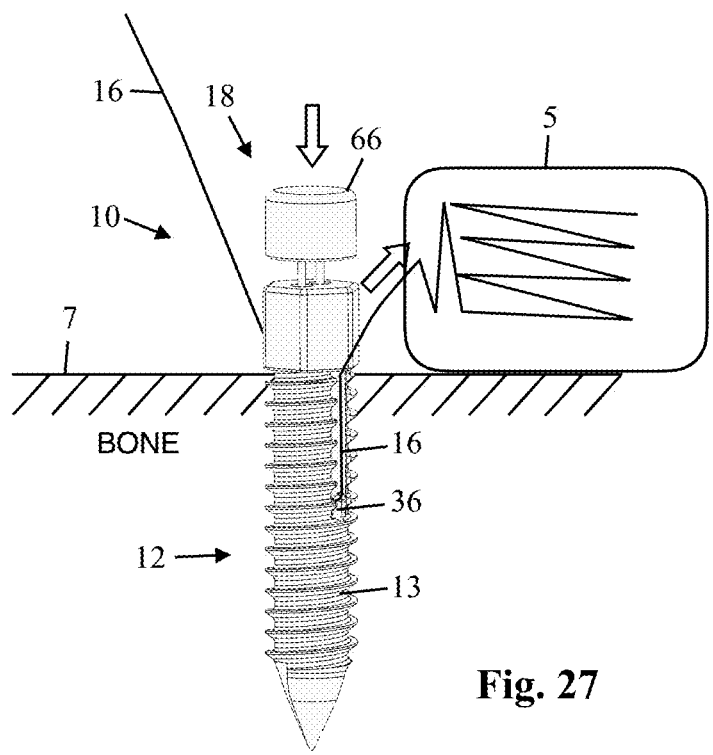
Figure 28:
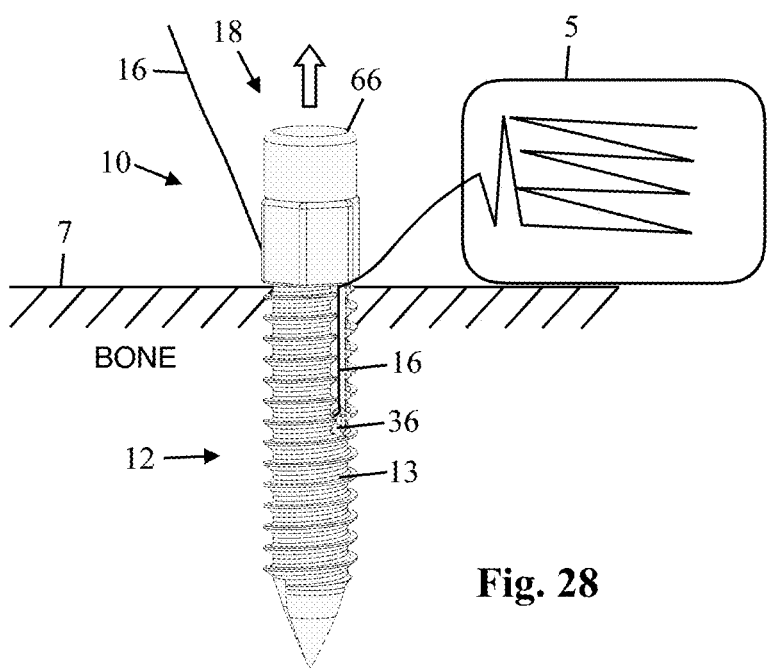
Figure 29:
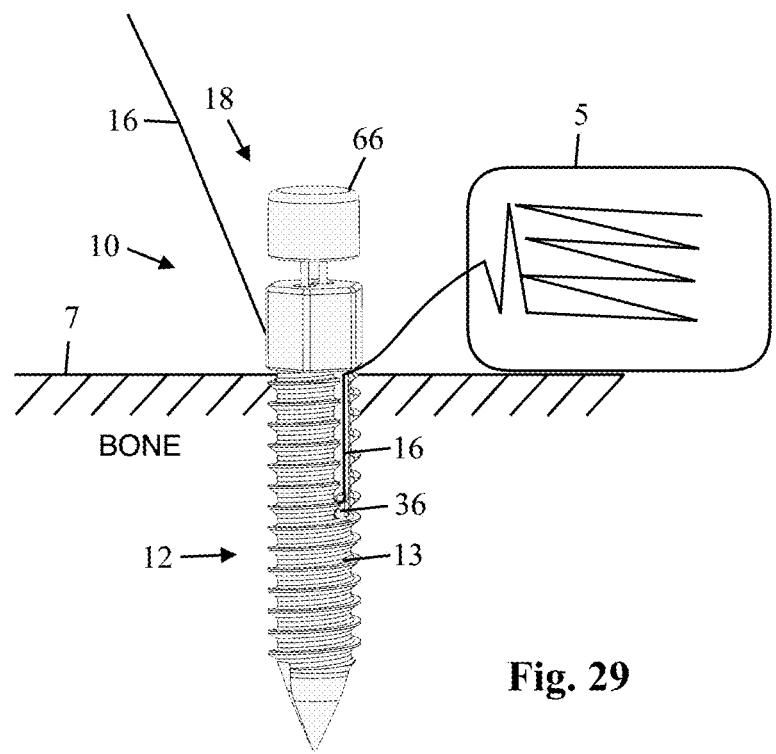
Figure 30:
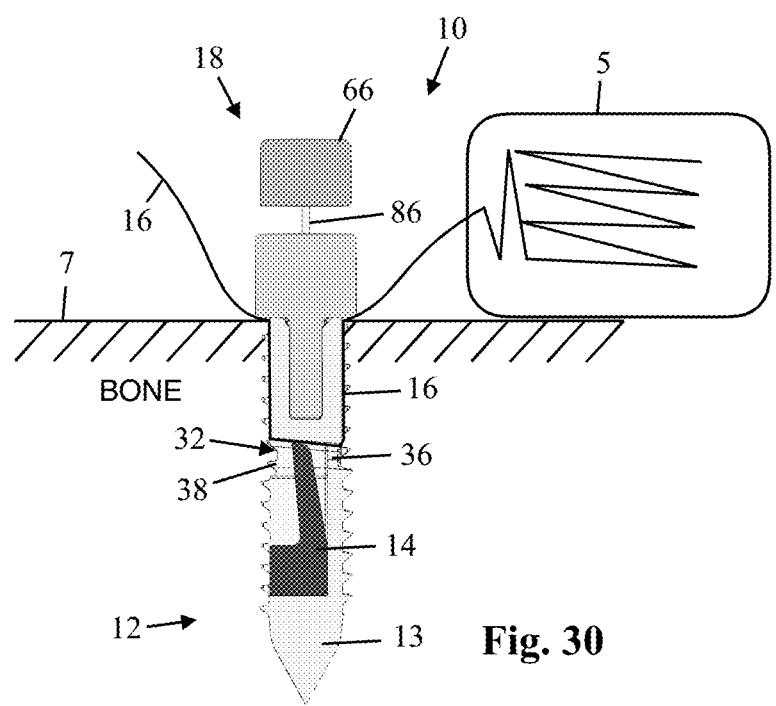
Figure 31:
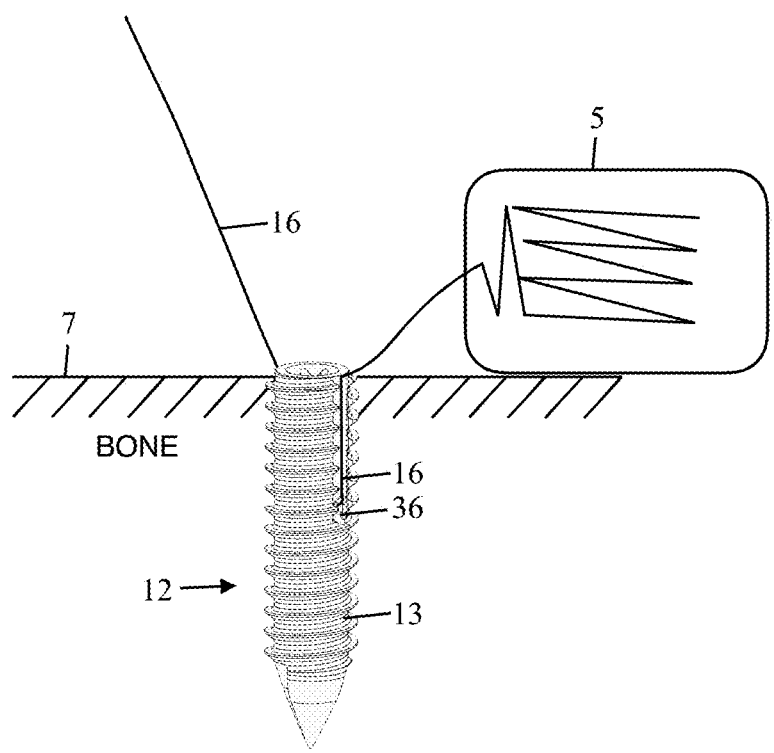

In some embodiments, the next step 108 of the method 100 is to optionally adjust the tension in the tensionable fixation member 16 by depressing the button 66 (e.g., manually or mechanically) of the release member 18 to engage the prongs 86 with the locking element 14 as described above to move the locking element from a locked position to an unlocked position and release the tensionable fixation member 16, as shown by way of example in FIGS. 27-28. By way of example, this allows the tensionable fixation member 16 to be pulled in the opposite direction (e.g., back through the transverse passage 32 and out of the ingress opening 36) to release tension in the tensionable fixation member 16.

Once the tensionable fixation member 16 has been re-tensioned to the user's satisfaction, the next step 110 of the method 100 is to lock the tensionable fixation member 16 in place by releasing the button 66 (e.g., manually or mechanically) of the release member 18 so that the prongs 86 retreat into the base 64 of the release member 18 and the locking element 14 returns to its initial locked position, capturing or pinching the tensionable fixation member 16 as described above, as shown by way of example in FIGS. 29-30.

By way of example, the next step 112 of the method 100 is to decouple the release member 18 and/or insertion tool from the anchor assembly 12 and removing the release member 18 and/or insertion tool from the surgical field. Once the tissue has been repaired and the tools or accessories removed, the user may then close the operative wound.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention. As used herein, the term "tensionable" means capable of being longitudinally stretched or strained to achieve a desired degree of tension.

The system and method disclosed herein has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all sub-ranges and individual values are intended to be encompassed. This invention is not to be limited by the embodiments disclosed, including any shown in the drawings or exemplified in the specification, which are given by way of example and not of limitation. Additionally, it should be understood that the various embodiments of the re-tensionable anchor system and related methods described herein contain optional features that can be individually or together applied to any other embodiment shown or contemplated here to be mixed and matched with the features of that device.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:
1. A surgical anchor system for tensionable fixation members, comprising:
   an anchor assembly comprising a bone anchor and a locking element,
   the bone anchor comprising a cylindrical elongated anchor body having a central longitudinal axis, a proximal end, a distal end, a central portion located between the proximal end and distal ends, a bone engaging feature, a central cavity and a transverse passage extending through the central portion of the anchor body perpendicular to the central longitudinal axis and intersecting with the central cavity, the transverse passage having an ingress opening on one side of the anchor body and an egress opening on the opposite side of the anchor body;
   the locking element positioned within the central cavity and comprising a base immovably secured within the central cavity such that the base is prevented from any movement within the central cavity and a deflectable flange extending proximally from the base into the transverse passage, the deflectable flange having a proximal engagement portion;

a tensionable fixation member coupled with the anchor assembly, the tensionable fixation member extending through the transverse passage and having a first end configured for attachment to a tissue, bone, or other member and a second, free end; and a release member comprising an actuator and an elongated extension, the actuator operable to translate the elongated extension so that the elongated extension engages the locking element to move the locking element from a first, locked position to a second, unlocked position;

wherein the deflectable flange has an angular bias in the direction of the egress opening that allows translation of the tensionable fixation member through the transverse passage in the direction of the egress opening and prevents translation of the tensionable fixation member through the transverse passage in the direction of the ingress opening when the locking element is in the locked position; and wherein the deflectable flange is deflected in the direction of the egress opening by the elongated extension upon operation of the release member, allowing translation of the tensionable fixation member through the transverse passage in the direction of the ingress opening when the locking element is in the unlocked position.

2. The system of claim 1, wherein the bone engaging feature comprises a helical thread extending around an exterior surface of the anchor body.

3. The system of claim 1, wherein the anchor body further comprises a smooth, linear, external recess extending between the ingress opening and the proximal end.

4. The system of claim 1, wherein the anchor body further comprises a smooth, linear, external recess extending between the egress opening and the proximal end.

5. The system of claim 1, wherein the transverse passage comprises an angled proximal wall.

6. The system of claim 5, wherein the proximal portion of the deflectable flange and the angled proximal wall of the transverse passage cooperate to form a pinch point that captures the tensionable fixation member when the locking element is in the locked position.

7. The system of claim 1, wherein the tensionable fixation member is one of a surgical suture or tape.

8. The system of claim 1, wherein the release member is located on an insertion tool.

9. The system of claim 1, wherein the release member is temporarily coupled with the anchor assembly.

10. The system of claim 1, wherein the release member is mated with a driver recess formed in the proximal end of the anchor body.

11. The system of claim 1, wherein the base of the locking element is immovably secured to the central cavity by at least one of a form fit engagement, press fit engagement, snap fit engagement, adhesive, pin, and screw.

* * * * *